United States Patent [19]
McDowell

[11] Patent Number: 5,797,916
[45] Date of Patent: Aug. 25, 1998

[54] TROCHANTERIC REATTACHMENT CERCLAGE DEVICE

[75] Inventor: Christopher S. McDowell, Bridgewater, Mass.

[73] Assignee: Johnson & Johnson Professional, Inc., Raynham, Mass.

[21] Appl. No.: 763,541

[22] Filed: Dec. 10, 1996

[51] Int. Cl.$^6$ .................................................. A61B 17/82
[52] U.S. Cl. ......................................... 606/74; 606/69
[58] Field of Search ............................ 606/69, 70, 71, 606/72, 74, 86, 103

[56] References Cited

U.S. PATENT DOCUMENTS

| | | | |
|---|---|---|---|
| 1,950,799 | 3/1934 | Jones | 606/74 |
| 4,269,180 | 5/1981 | Dall et al. | 128/92 |
| 4,473,068 | 9/1984 | Oh | 128/92 |
| 4,512,346 | 4/1985 | Lemole | 128/335 |
| 4,565,193 | 1/1986 | Streli | 128/92 |
| 4,651,724 | 3/1987 | Berentey et al. | 128/92 |
| 4,889,110 | 12/1989 | Galline et al. | 606/69 |
| 4,896,668 | 1/1990 | Popoff et al. | 606/74 |
| 5,190,545 | 3/1993 | Corsi et al. | 606/74 |
| 5,324,291 | 6/1994 | Ries et al. | 606/71 |
| 5,376,126 | 12/1994 | Lin | 623/23 |
| 5,415,658 | 5/1995 | Kilpela et al. | 606/57 |
| 5,462,542 | 10/1995 | Alesi, Jr. | 606/151 |
| 5,611,801 | 3/1997 | Songer | 606/73 |

*Primary Examiner*—Michael Buiz
*Assistant Examiner*—David O. Reip
*Attorney, Agent, or Firm*—Nutter, McClennen & Fish, LLP

[57] ABSTRACT

A bone fixation device is provided that includes a retaining member fabricated from a biocompatible material. First and second biocompatible cables are permanently secured at one end to respective first and second sides of the retaining member. A cable crimp is used to bind the free portions of the first and second cables. Cable guides on the retaining member establish an alignment angle for the cables with respect to the longitudinal axis of the retaining member. The retaining member can include gripping members.

18 Claims, 2 Drawing Sheets

TROCHANTERIC REATTACHMENT CERCLAGE DEVICE

CROSS-REFERENCE TO RELATED APPLICATION

--Not Applicable --

STATEMENT REGARDING FEDERALLY SPONSORED RESEARCH

-- Not Applicable --

FIELD OF THE INVENTION

The present invention relates to a medical implant, and more particularly to a bone reattachment device.

BACKGROUND OF THE INVENTION

Various orthopaedic procedures entail the use of wires and plates to reinforce and splint bones that are fragmented due to traumatic injury or deliberately severed during an arthroplasty procedure. For example, during some hip arthroplasty procedures the greater trochanter is separated from the proximal end of the femur so that soft tissue attached to the greater trochanter can be moved aside in preparation for implantation of a femoral stem. After the femoral stem is seated within the medullary canal of the femur, the greater trochanter is reattached to the proximal end of the femur. Because the greater trochanter is subjected to considerable stress during ambulation, mechanical reinforcement of this bone portion is necessary.

Bone reattachment techniques can require bone screws or pins to hold bone portions together. With respect to hip arthroplasty, a bolt and a washer can be used to secure the greater trochanter to a femoral stem adapted to receive the bolt. Other binding or reinforcement devices include a structure through which wires are threaded to bind the greater trochanter to the femur. With respect to the wire or cerclage devices, each of several wires or cables are independent of the structure (i.e., not attached to the structure before the operation) and must be secured to the structure during the surgical procedure. Use of these devices entails tedious manipulation of the wires to correctly position them and to attach them to the structure in situ. Not only can it be difficult to hold the structure and the wires in a required position while loose ends of the wire are manipulated, but it can be inconvenient or clinically disadvantageous to perform cable tightening and/or securing on or near the structure.

For example, U.S. Pat. No. 4,269,180 discloses a device that is configured for reattachment of the greater trochanter to the proximal end of the femur. However, the device shares deficiencies with the previously discussed devices in that it has holes through which both ends of a free wire must be threaded. Following the threading of the wires into the body of the device, a central portion of the device must be crimped to secure the wires.

SUMMARY OF THE INVENTION

The present invention overcomes disadvantages of known bone reattachment or fixation devices by providing a bone fixation device with integral cerclage cables that may be extended from the device at a predetermined angle to ensure proper encirclement of a bone. Because the cables and the fixation device form a unified element, the cables can be quickly, easily and properly positioned. Binding the free cable ends together, such as by crimping, can be performed at selected locations away from a bone retaining structure of the bone fixation device.

In an exemplary embodiment of the invention, a bone fixation device includes a retaining member fabricated from a biocompatible material. The retaining member has a first side, a second side, and a bone engaging face. First and second cables are secured to the first and second sides, respectively. A cable crimp can be provided to bind the first cable to the second cable. First and second cable guides can be provided to align the respective first and second cables at an angle with respect to the longitudinal axis of the retaining member. Gripping members can extend from the retaining member; and the gripping members can include barbs to enhance fixation to a bone surface onto which the retaining member is placed. In addition to, or instead of barbs, the bone engaging face of the retaining member can include a textured surface portion. The retaining member can further include a hole through which a fixation member is insertable.

BRIEF DESCRIPTION OF THE DRAWINGS

A more complete understanding of the present invention and the attendant advantages and features thereof will be more readily understood by reference to the following detailed description when it is considered in conjunction with the accompanying drawings wherein.

DETAILED DESCRIPTION OF THE INVENTION

Figure 1:
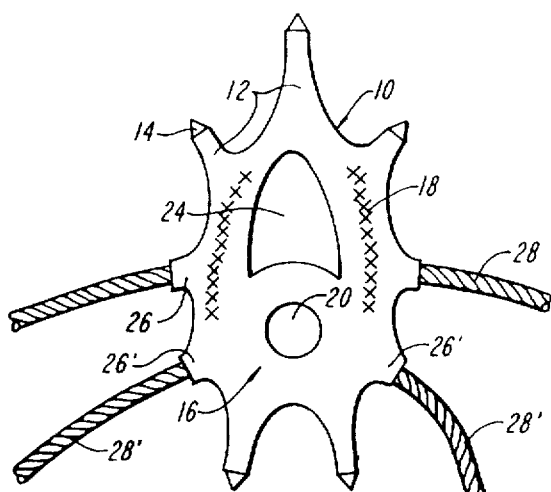
FIG. 1 is a perspective view of the bone fixation device in accordance with the invention.

FIG. 1 illustrates a bone fixation device that is specifically configured for reattachment of the greater trochanter to the proximal end of a femur from which it has been severed. The device includes a body portion or retaining member 10 from which extend elongate retaining or gripping members 12 that define the periphery of the retaining member. One or more of the gripping members 12 include spikes, points, or barbs 14 that readily penetrate the relatively soft bone of the greater trochanter when pressure is applied to the barbs. In addition to or instead of barbs 14 on or near the ends of the gripping members 12, the entire bone engaging surface 16 of the retaining member 10, or a portion thereof, can include roughened or textured regions 18. The barbs 14 and/or textured regions 18 engage the outer surface of the greater trochanter to inhibit slippage or movement of the retaining member 10 with respect to the outer surface of the trochanter onto which it is placed.

In an exemplary embodiment, the retaining member 10 includes five elongated gripping members 12, wherein each gripping member includes a 1 mm barb 14 at its distal end. In the embodiment illustrated in FIG. 1, three gripping members extend from a first end of the retaining member 10, wherein the top center gripping member 12 is longer than the adjacent, flanking gripping members and wherein the top center gripping member is substantially aligned with the longitudinal axis of the retaining member. Two gripping members 12 extend from a second end of the retaining member 10. Other embodiments of the retaining member 10, include more or less than five gripping members 12 and include barbs 14 that are longer or shorter than 1 mm. The bone engaging surface 16 of the retaining member 10 and the gripping members 12 can be shaped as required for particular arthroplasty procedures. For embodiments of the fixation device that include a textured region 18, the textured region can be a grit blasted surface or an as cast macrotexture that encourage bone ingrowth.

Figure 1A:
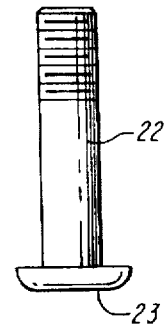
FIG. 1A is a view of a bolt that is suitable for engaging the bone fixation device of FIG. 1.

Referring to FIGS. 1 and 1A, an optional hole 20 through the retaining member 10 can be provided to locate, align, and/or guide a trochanteric bolt, screw or other fixation member 22 with respect to the greater trochanter and/or a femoral stem. The retaining member 10 can be fabricated from titanium alloys such as Ti-6Al-4V, cobalt chrome (CrCo), stainless steel, or any other biocompatible metal or metal alloy. Biocompatible plastics can also be employed. In an illustrative embodiment, represented by FIG. 1A, the fixation member 22 is a bolt having an expanded head 23 adapted to engage the face opposite the bone engaging face when the bolt is inserted through the hole from the second face. Instead of, or in addition to the hole 20, the retaining member 10 can include a cutout region 24 and/or perforations therethrough. Not only does the cutout region 24 reduce the weight of the device, as well as its cost, but it also permits fibrous tissue to grow in and around the cutout to further stabilize and secure the retaining member 10 to the trochanter.

The retaining member 10 that is illustrated in FIG. 1 includes four cable guides 26, 26'. Cables 28, 28' extend from each cable guide 26, 26'. Each cable 28, 28' has a fixed end and a free end, wherein the cable guides 26, 26' establish a permanent, pre-operative junction between the fixed end of each of the cables 28, 28' and the retaining member 10. The cable guides 26, 26' can be oriented, or cause the cables 28, 28' to be oriented, at a predetermined angulation with respect to other cables or with respect to the retaining member 10. For example, the embodiment of the bone fixation device illustrated in FIG. 1 includes a first pair of opposed cable guides 26 that orients the associated cables 28 at slightly less than 90 degrees with respect to the longitudinal axis of the retaining member 10. A second pair of opposed cable guides 26' positions the associated cables 28' at much less than 90 degrees with respect to the longitudinal axis of the retaining member 10. Angulation of one or more of the cables 28 with respect to the retaining member 10 allows stress to be applied to the femur and trochanter in a direction that improves reapproximation of the greater trochanter to the remainder of the femur. However, if desired, the cable guides 26, 26' can align the respective cables 28, 28' at approximately 90 degrees with respect to the longitudinal axis of the retaining member.

As used herein, "cable" is intended to encompasses any elongate flexible member, such as a plastic band or strip, a solid wire, or braided wires. The cable can include exposed biocompatible metal or be covered with a biocompatible plastic. In an exemplary embodiment, the cables are braided cobalt chrome or stainless steel wire.

Figure 2:
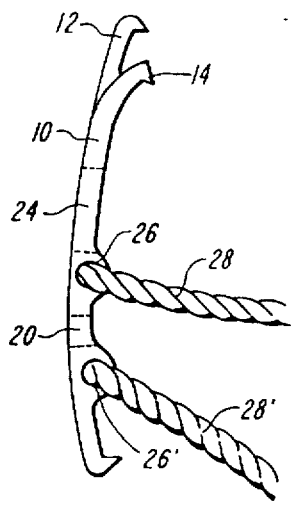
FIG. 2 is a side view of the bone fixation device illustrated in FIG. 1.

FIG. 2 is a side view of the bone fixation device shown in FIG. 1. In this illustration, the concave curvature of the retaining member 10 and the gripping members 12 are clearly evident. In the illustrated embodiment, the gripping members 12 that flank the top center gripping member have an even more pronounced curvature than the top center gripping member to allow better conformity with the curved face of the greater trochanter. Additionally, the retaining member 10 can have a double concave or bowl-like shape to conform to the shape of the trochanter.

Figure 3:
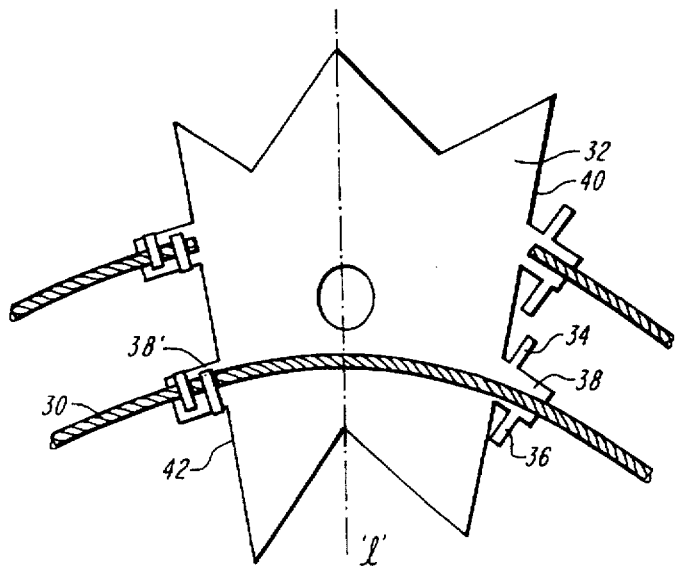
FIG. 3 depicts an alternative embodiment of the fixation device.

Referring now to FIG. 3, an embodiment of the bone fixation device is shown that illustrates a securing structure for affixing a cable 30 to a retaining member 32. In this embodiment, the securing structure includes first and second malleable tabs 34 and 36 that extend from an angled cable guide 38. A cable 30 traverses the retaining member 32 and passes between the tabs 34 and 36. The tabs can be bent over the cable 30 and crimped tightly to render the cable immovable with respect to the retaining member 32 proximate the cable guide 38. A second cable guide 38' shown tabs in a bent or crimped position. Other embodiments of the securing structure include a single tab or more than two tabs.

The securing structure can include a passage through the retaining member that includes an integral locking device or a deformable portion of the retaining member capable of trapping a portion of a cable therein. Alternatively, the securing structure can include a socket in the retaining member into which one end of the cable is bonded with heat or an adhesive material. Furthermore, a single cable can traverse the retaining member and thus extend from opposing cable guides; or individual cables can be associated with each cable guide. For descriptive purposes, a single cable that extends from two opposing cable guides can be characterized as two cables. Many other techniques for permanently attaching a cable to a retaining member are within the scope of knowledge of one skilled in the art; and the technique for securing a cable to the retaining member is not a limitation of the invention. However, the invention does require that one or more cables be permanently attached, pre-operatively, to the retaining member.

Comparing the embodiment of the retaining member illustrated in FIG. 1 with the embodiment illustrated in FIG. 3, it should be noted that whereas the embodiment of FIG. 1 includes scalloped sides, the embodiment of FIG. 3 includes substantially straight sides 40 and 42 which are not parallel to each other or to the longitudinal axis "1" of the retaining member.

Figure 4:
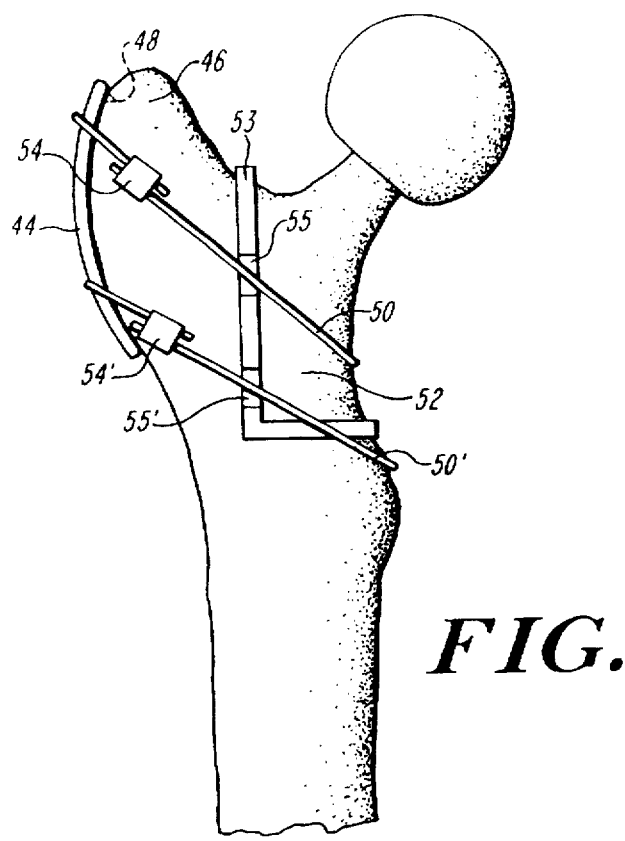
FIG. 4 illustrates the fixation device secured to a femur.

Referring now to FIG. 4, an embodiment of the bone fixation device is shown in an installed configuration. A retaining member 44 conforms to the surface shape of the greater trochanter 46 and barbs 48 penetrate the soft surface of the greater trochanter. Cables 50 and 50' are secured to the retaining member 44 and encircle the greater trochanter and a femoral stem 52. Cables 50 and 50' are joined by cable crimps 54 and 54' using conventional cerclage cable tightening and crimping tools (not shown). Excess cable is removed. FIG. 4 clearly illustrates angulation of the cables 50 and 50' with respect to the retaining member 44. To further ensure correct angulation of the cables 50 and 50', the femoral stem 52 can include a flange 53 having notches 55 and 55' that are shaped to receive and to guide cables 50 and 50', respectively.

As used herein, "cable crimp" is intended to encompass any structure known to those skilled in the art for joining cables and wires. Thus, the cable crimp can include deformable elements, clamps, screw locks, spring locks and the like. For an embodiment of the invention wherein the cables are notched plastic strips, the cable crimp and be a unidirectional engagement device such as the lock on a zip tie.

Figure 5:
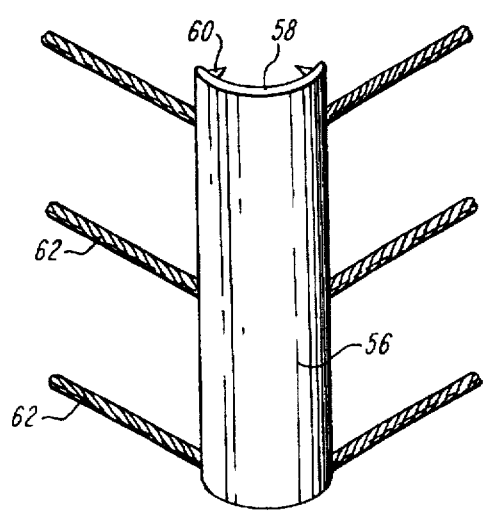
FIG. 5 illustrates an alternative embodiment of the invention.

Although the invention has been described with respect to reattachment of the greater trochanter to the femur, the invention is readily adaptable to other applications, and the shape of the retaining member, as well as the number and position of cerclage cables can be adapted as desired. For example, FIG. 5 illustrates a retaining member 56 that is configured as an elongate plate. The retaining member 56 can include a curved face 58 that is adapted for conformal fit against a bone surface. As described with respect to the previous embodiments, the retaining member 56 can include one or more barbs 60 to enhance bone fixation and/or a textured surface. Cables 62 are permanently secured to the retaining member 56 in opposing pairs and are securable to each other at a location separated from the retaining member after the cable has encircled a bone or implant structure. Even if the retaining member is configured as a circle, halves (sides) of the circular member can be provided with opposing cerclage cables. Thus, the specific shape of the retaining member is not to be considered a limitation of the invention.

As used herein, "side" can refers to the edge(s) of the retaining member between the bone engaging face and the face opposite the bone engaging face. Thus, cables can be inserted into or extend from such a surface. However, "side" also refers to the portions of the retaining member separated by the longitudinal axis of the retaining member. Cables can be secured to either or both of these sides on either the bone engaging face or the opposing face and still be described as being secured to a side.

Although the invention has been shown and described with respect to exemplary embodiments thereof, various other changes, omissions and additions in form and detail thereof may be made without departing from the spirit and scope of the invention. All references cited herein are expressly incorporated by reference in their entirety.

What is claimed is:

1. A bone fixation device comprising:
   a retaining member fabricated from a biocompatible material, the retaining member having a first side, a second side, and a bone engaging face;
   a first cable having a first end and a second end, the first end of the first cable being permanently secured to the first side of the retaining member at a first junction;
   a second cable having a first end and a second end, the first end of the second cable being permanently secured to the second side of the retaining member at a second junction;
   a first cable guide proximate the first junction and extending from the first side of the retaining member; and
   a second cable guide proximate the second junction and extending from the second side of the retaining member.

2. The bone fixation device of claim 1, further comprising a cable crimp adapted to bind the first cable to the second cable.

3. The bone fixation device of claim 1, wherein the retaining member has a longitudinal axis and wherein the first cable guide and the second cable guide align the respective first and second cables at an angle with respect to the longitudinal axis that is approximately 90 degrees.

4. The bone fixation device of claim 1, wherein the retaining member has a longitudinal axis and wherein the first cable guide and the second cable guide align the respective first and second cables at an angle with respect to the longitudinal axis that is less than 90 degrees.

5. The bone fixation device of claim 1, wherein the retaining member includes:
   a first securing structure for permanently securing the first cable to the first side of the retaining member; and
   a second securing structure for permanently securing the second cable to the second side of the retaining member.

6. The bone fixation device of claim 5, wherein each of the first and second securing structures includes a malleable tab which is crimpable over the respective cable ends to secure the respective cable to the retaining member.

7. The bone fixation device of claim 1, further including a plurality of gripping members extending from the retaining member.

8. The bone fixation device of claim 7, wherein each of the gripping members includes a barb.

9. The bone fixation device of claim 8, wherein each barb of the gripping members is approximately 1 mm long.

10. The bone fixation device of claim 1, further comprising a plurality of barbs projecting from the bone engaging face of the retaining member.

11. The bone fixation device of claim 1, wherein the bone engaging face includes a textured portion.

12. The bone fixation device of claim 1, wherein the retaining member includes a second face opposite the bone engaging face, the second face and the bone engaging face defining an aperture therebetween; and further including a bolt having a shank and an expanded head, wherein the shank is insertable through the aperture from the second face and wherein the expanded head engages the second face.

13. The bone fixation device of claim 1, further comprising:
   a third cable having a first end and a second end, the first end of the third cable being permanently secured to the first side of the retaining member; and
   a fourth cable having a first end and a second end, the first end of the fourth cable being permanently secured to the second side of the retaining member;
   wherein the bone engaging surface forms a concave surface, and wherein the first cable is angled toward the third cable and the second cable is angled toward the fourth cable.

14. The bone fixation device of claim 13, wherein the retaining member includes a first end from which extend three gripping members and a second end from which extend two gripping members.

15. The bone fixation device of claim 14, wherein one of the gripping members is substantially aligned with the longitudinal axis of the retaining member.

16. The bone fixation device of claim 14, wherein at least one gripping member has a greater amount of concave curvature than the other gripping members.

17. A bone fixation device comprising:
   a retaining member fabricated from a biocompatible material, the retaining member having a first side, a second side, and a bone engaging face;
   a first cable having a first end and a second end, the first end of the first cable being permanently secured to the first side of the retaining member at a junction;
   a second cable having a first end and a second end, the first end of the second cable being permanently secured to the second side of the retaining member at a junction;
   a first cable crimp adapted to bind the first cable to the second cable;
   a first cable guide proximate the junction of the first cable and extending from the first side of the retaining member;
   a second cable guide proximate the junction of the second cable and extending from the second side of the retaining member; and a plurality of gripping members extending from the retaining member.

18. A bone fixation device comprising:

a retaining member fabricated from a biocompatible material, the retaining member having a first side, a second side, and a bone engaging face;

a first cable having a first end and a second end, the first end of the first cable being permanently secured to the first side of the retaining member at a junction;

a second cable having a first end and a second end, the first end of the second cable being permanently secured to the second side of the retaining member at a junction;

a third cable having a first end and a second end, the first end of the third cable being permanently secured to the first side of the retaining member at a junction; and a fourth cable having a first end and a second end, the first end of the fourth cable being permanently secured to the second side of the retaining member at a junction;

a first cable crimp adapted to bind the first cable to the second cable;

a second cable crimp adapted to bind the third cable to the fourth cable;

a first cable guide proximate the junction of the first cable and the first side of the retaining member;

a second cable guide proximate the junction of the second cable and the second side of the retaining member;

a third cable guide proximate the junction of the third cable and the first side of the retaining member;

a fourth cable guide proximate the junction of the second cable and the second side of the retaining member; and a plurality of gripping members extending from the retaining member, each of the gripping members including a barb, and one of the gripping members being substantially aligned with the longitudinal axis of the retaining member.

* * * * *